(12) United States Patent
Ward et al.

(10) Patent No.: US 8,636,711 B2
(45) Date of Patent: Jan. 28, 2014

(54) STABILIZED GLUCAGON SOLUTIONS AND USES THEREFOR

(75) Inventors: W. Kenneth Ward, Portland, OR (US); Richard D. DiMarchi, Bloomington, IN (US)

(73) Assignees: Legacy Emanuel Hospital & Health Center, Portland, OR (US); Indian University Research and Technology Corporation, Indianapolis, IN (US)

(*) Notice: Subject to any disclaimer, the term of this patent is extended or adjusted under 35 U.S.C. 154(b) by 222 days.

(21) Appl. No.: 13/160,349

(22) Filed: Jun. 14, 2011

(65) Prior Publication Data

US 2012/0071817 A1 Mar. 22, 2012

Related U.S. Application Data

(60) Provisional application No. 61/354,457, filed on Jun. 14, 2010.

(51) Int. Cl.
*A61M 31/00* (2006.01)

(52) U.S. Cl.
USPC ............................................. 604/504; 604/65

(58) Field of Classification Search
USPC ...................................... 604/65–67; 600/365
See application file for complete search history.

(56) References Cited

U.S. PATENT DOCUMENTS

| | | | |
|---|---|---|---|
| 4,245,634 A | 1/1981 | Albisser et al. | |
| 4,431,004 A | 2/1984 | Bessman et al. | |
| 4,515,584 A | 5/1985 | Abe et al. | |
| 4,822,337 A | 4/1989 | Newhouse et al. | |
| 5,062,841 A | 11/1991 | Siegel | |
| 5,109,866 A | 5/1992 | Guegan et al. | |
| 5,165,407 A | 11/1992 | Wilson et al. | |
| 5,569,186 A | 10/1996 | Lord et al. | |
| 5,702,444 A | 12/1997 | Struthers et al. | |
| 5,711,861 A | 1/1998 | Ward et al. | |
| 5,741,330 A | 4/1998 | Brauker et al. | |
| 5,820,622 A | 10/1998 | Gross et al. | |
| 5,885,616 A | 3/1999 | Hsiao et al. | |
| 5,995,860 A | 11/1999 | Sun et al. | |
| 6,001,067 A | 12/1999 | Shults et al. | |
| 6,049,727 A | 4/2000 | Crothall | |
| 6,056,734 A | 5/2000 | Jacobsen et al. | |
| 6,121,009 A | 9/2000 | Heller et al. | |
| 6,122,535 A | 9/2000 | Kaestle et al. | |
| 6,212,416 B1 | 4/2001 | Ward et al. | |
| 6,233,471 B1 | 5/2001 | Berner et al. | |
| 6,442,413 B1 | 8/2002 | Silver | |

(Continued)

OTHER PUBLICATIONS

Knobbe et al., "The Extended Kalman Filter for Continuous Glucose Monitoring", Diabetes Technology and Therapeutics, Feb. 2005, vol, 7, No. 1, pp. 15-27.

(Continued)

*Primary Examiner* — Nicholas Lucchesi
*Assistant Examiner* — Melissa A Snyder
(74) *Attorney, Agent, or Firm* — Kolisch Hartwell, P.C.

(57) ABSTRACT

Stabilized glucagon solutions, methods of storing and using the stabilized glucagon solutions, and drug delivery devices containing the stabilized glucagon solutions. In some embodiments, the glucagon solutions may be alkaline, such as with a pH of at least about 9. The glucagon solutions may be resistant to aggregation of glucagon when the solutions are stored for a prolonged period, such as at least about three days, at room temperature and/or physiological temperature.

20 Claims, 6 Drawing Sheets

(56) References Cited

U.S. PATENT DOCUMENTS

| | | | |
|---|---|---|---|
| 6,463,321 | B2 | 10/2002 | Granger |
| 6,466,810 | B1 | 10/2002 | Ward et al. |
| 6,477,395 | B2 | 11/2002 | Schulman et al. |
| 6,484,046 | B1 | 11/2002 | Say et al. |
| 6,485,437 | B1 | 11/2002 | Tapper |
| 6,512,939 | B1 | 1/2003 | Colvin et al. |
| 6,514,718 | B2 | 2/2003 | Heller et al. |
| 6,544,212 | B2 | 4/2003 | Galley et al. |
| 6,558,351 | B1 | 5/2003 | Steil et al. |
| 6,565,509 | B1 | 5/2003 | Say et al. |
| 6,572,545 | B2 * | 6/2003 | Knobbe et al. ............ 600/365 |
| 6,740,072 | B2 | 5/2004 | Starkweather et al. |
| 7,433,727 | B2 | 10/2008 | Ward et al. |
| 8,114,023 | B2 | 2/2012 | Ward et al. |
| 2001/0020137 | A1 | 9/2001 | Granger |
| 2002/0120186 | A1 | 8/2002 | Keimel |
| 2003/0130616 | A1 | 7/2003 | Steil et al. |
| 2005/0027181 | A1 | 2/2005 | Goode, Jr. et al. |
| 2005/0043598 | A1 | 2/2005 | Goode, Jr. et al. |
| 2005/0192557 | A1 | 9/2005 | Brauker et al. |
| 2006/0178304 | A1 * | 8/2006 | Juul-Mortensen et al. ..... 514/12 |

OTHER PUBLICATIONS

Zisser et al., "Run-to-Run Control of Meal-Related Insulin Dosing", Diabetes Technology and Therapeutics, 2005, vol. 7, No. 1, pp. 48-57.

Gopakumaran et al., "A Novel Insulin Delivery Algorithm in Rats with Type 1 Diabetes: The Fading Memory Proportional-Derivative Method", Artificial Organs, 2005, vol. 29, No. 8, pp. 599-607.

Kadish, A.H., "Automation Control of Blood Sugar: I. A Servo-mechanism for Glucose Monitoring and Control", The American Journal of Medical Electronics, 1964, vol. 39, pp. 82-86.

Pagurek et al., "Adaptive Control of the Human Glucose-Regulatory System", Medical and Biological Engineering and Computing, 1972, vol. 10, No. 6, pp. 752-761.

Pfeiffer et al., "The Artificial Beta Cell—a Continuous Control of Blood Sugar by External Regulation of Insulin Infusion (Glucose Controlled Insulin Infusion System)", Hormone Metabolic Research, 1974, vol. 6, No. 5, pp. 339-342.

Albisser et al., "An Artificial Endocrine Pancreas", Diabetes, May 1974, vol. 23, No. 5, pp. 389-396.

Kraegen et al., "Control of Blood Glucose in Diabetics using an Artificial Pancreas", Australian and New Zealand Journal of Medicine, 1977, vol. 7, No. 3, pp. 280-286.

Marliss et al., "Normalization of Glycemia in Diabetics during Meals with Insulin and Glucagon Delivery by the Artificial Pancreas", Diabetes, Jul. 1977, vol. 26, No. 7, pp. 663-672.

Clemens, AH., "Control Algorithms for Artificial Beta Cell", Hormone Metabolic Research Supplement Series, 1979, vol. 8, pp. 35-38.

Clemens, AH., "Feedback Control Dynamics for Glucose Controlled Insulin Infusion System", Medical Progress through Technology, 1979, vol. 6, No. 3, pp. 91-98.

Goriya et al., "The Development of an Artificial Beta Cell System and its Validation in Depancreatized Dogs: the Physiological Restoration of Blood Glucose Homeostasis", Medical Progress through Technology, 1979, vol. 6, No. 3, pp. 99-108.

Verdonk et al., "Glucose Clamping using the Biostator GCIIS", Hormone Metabolic Research, Apr. 1980, vol. 12, No. 4, pp. 133-135.

Broekhuyse et al, "Comparison of Algorithms for the Closed-Loop Control of Blood Glucose Using the Artificial Beta Cell", IEEE Transactions on Biomedical Engineering, Oct. 1981, vol. BME-28, issue 10, pp. 678-687.

Clemens et al., "Development of the Biostator Glucose Clamping Algorithm", Clinical Chemistry, 1982, vol. 28, No. 9, pp. 1899-1904.

Mayfield et al., "Predicting Insulin Requirements for a Portable Insulin Pump using the Biostator: Evidence for Reversible Insulin Resistance in Poorly Controlled Type I Diabetics", Diabetes, Oct. 1983, vol. 32, No. 10, pp. 908-914.

Cobelli et al., "Evaluation of Portal/Peripheral Route and of Algorithms for Insulin Delivery in the Closed-Loop Control of Glucose in Diabetes—A Modeling Study", IEEE Transactions on Biomedical Engineering , Feb. 1983, vol. BME-30, issue 2, pp. 93-103.

Shichiri et al., "Closed-Loop Glycemic Control with a Wearable Artificial Endocrine Pancreas: Variations in Daily Insulin Requirements to Glycemic Response", Diabetes, Dec. 1984, vol. 33, No. 12, pp. 1200-1202.

Nomura et al., "A Mathematical Insulin-Secretion Model and Its Validation in Isolated Rat Pancreatic Islets Perifusion", Computers Biomedical Research, 1984, vol. 17, pp. 570-579.

Ward et al., "Diminished B Cell Secretory Capacity in Patients with Noninsulin-Dependent Diabetes Mellitus", The Journal of Clinical Investigation, Oct. 1984, vol. 74, No. 4, pp. 1318-1328.

Fischer et al., "In Vivo Comparison of Different Algorithms for the Artificial Beta-Cell", Artifical Organs, May 1985, vol. 9, No. 2, pp. 173-179.

Rebrin et al., "Automated Feedback Control of Subcutaneous Glucose Concentration in Diabetic Dogs", Diabetologia, Aug. 1989, vol. 32, No. 8, pp. 573-576.

Hosker et al., "Similar Reduction of First- and Second-Phase B-Cell Responses at Three Different Glucose Levels in Type II Diabetes and the Effect of Gliclazide Therapy", Metabolism, Aug. 1989, vol. 38, No. 8, pp. 767-772.

Rousseeuw, Peter J., "Handbook of Statistical Methods for Engineers and Scientists: Robust Estimation and Identifying Outliers", 1990, Chapter 16, pp. 16.1-16.24, Free University Press Brussels, Belgium.

Laury et al., "Differential Effects of Prolonged Hyperglycemia on in Vivo and in Vitro Insulin Secretion in Rats", Endocrinology, 1991, vol. 128, No. 5, pp. 2526-2533.

Reboldi et al., Time Delay Compensation for Closed-Loop Insulin Delivery Systems: A Simulation Study, The International Journal of Artificial Organs, Jun. 1991, vol. 14, No. 6, pp. 350-358.

Kientz et al., A Robust Controller for Insulin Pumps Based on H-infinity Theory, IEEE Transactions on Biomedical Engineering, Nov. 1993, vol. 40, No. 11, pp. 1133-1137.

Wolf et al., "Angiotensin II-Stimulated Expression of Transforming Growth Factor Beta in Renal Proximal Tubular Cells: Attenuation after Stable Transfection with the C-Mas Oncogene", Kidney International, 1993, vol. 48, pp. 1818-1827.

Abramovitch, D., "Some Crisp Thoughts on Fuzzy Logic", American Controls Conference, 1994, vol. 1 pp. 168-172, Baltimore, MD.

Levenston et al., "The Role of Loading Memory in Bone Adaptation Simulations", Bone, Mar.-Apr. 1994, vol. 15, No. 2, pp. 177-186.

Candas et al., "An Adaptive Plasma Glucose Controller Based on a Nonlinear Insulin/Glucose Model", IEEE Transactions on Biomedical Engineering, Feb. 1994, vol. 41, No. 2, pp. 116-124.

El-Shal et al., "A Control Algorithm for the Two-Dimensional Glucoregulatory System", International Journal of System Science, 1995, vol. 26, No. 3, pp. 499-513.

Shimoda et al., "Closed-Loop Subcutaneous Insulin Infusion Algorithm with a Short-Acting Insulin Analog for LongTerm Clinical Application of Wearable Artificial Endocrine Pancreas", Frontiers of Medical & Biological Engineering, 1997, vol. 8, No. 3, pp. 197-211.

O'Connor et al, "Fibrinogen-dependent Adherence of Macrophages to Surface Coated with Poly(ethylene oxide)/ Poly(propylene oxide) Triblock Copolymers", Annals New York Academy of Sciences, 1997, vol. 831, pp. 138-144.

Jaremko et al., "Advances Toward the Implantable Artificial Pancreas for Treatment of Diabetes", Diabetes Care, Mar. 1998, vol. 21, No. 3, pp. 444-450.

Trajanoski et al, "Simulation Studies on Neural Predictive Control of Glucose using the Subcutaneous Route", Computers Methods and Programs in Biomedicine, May 1998, vol. 56, No. 2, pp. 133-139.

Trajanoski et al, "Neural Predictive Controller for Insulin Delivery using the Subcutaneous Route", IEEE Transactions on Biomedical Engineering, Sep. 1998, vol. 45, No. 9, pp. 1122-1134.

Bequette, BW., "Practical Approaches to Nonlinear Control: A Review of Process Applications", Nonlinear Model-based Process Control, NATO ASI Series, Series E, 1998, vol. 353, pp. 3-32, R. Berber and C. Kravaris (eds.), Kluwer, Dordrecht.

(56) References Cited

OTHER PUBLICATIONS

Katou et al, "Procollagen-Positive Fibroblasts Predominantly Express Fibrogenic Growth Factors and Their Receptors in Human Encapsulation Process against Foreign Body", Journal of Pathology, 1998, vol. 186, pp. 201-208.

Khouw et al., "TGF-beta and bFGF Affect the Differentiation of Proliferating Porcine Fibroblasts into Myofibroblasts in Vitro", Biomaterials, 1999, vol. 20, pp. 1815-1822.

Parker et al., "A Model-Based Algorithm for Blood Glucose Control in Type I Diabetic Patients", IEEE Transactions on Biomedical Engineering, Feb. 1999, vol. 46, issue 2, pp. 148-157.

Rollins, Leo, "Robust Control Theory",18-849b Dependable Embedded Systems, Spring 1999.

Kan et al., "Novel Control System for Blood Glucose using a Model Predictive Method", American Society for Artificial Internal Organs, Nov.-Dec. 2000, vol. 46, No. 6, pp. 657-662.

Updike et al., "A Subcutaneous Glucose Sensor with Improved Longevity, Dynamic Range, and Stability of Calibration", Diatbetes Care, Feb. 2000, vol. 23, No. 2, pp. 208-214.

Hu et al, "Molecular Basis of Biomaterial-Mediated Foreign Body Reactions", Blood, Aug. 15, 2001, vol. 98, No. 4, pp. 1231-1238.

Roberts et al., "Is Smad3 a Major Player in Signal Transductions Pathways Leading to Fibrogenesis?", Thomas L. Petty 43rd Annual Aspen Lung Conference: Mechanisms of Pulmonary Fibrosis, Chest/ 120/1/Jul. 2001 Supplement, pp. 43S-47S.

Ward et al., "The Effect of Microgeometry, Implant Thickness and Polyurethane Chemistry on the Foreign Body Response to Subcutaneous Implants", Biomaterials, 2002, vol. 23, pp. 4185-4192.

Chee et al, "Closed-Loop Glucose Control in Critically Ill Patients Using Continuous Glucose Monitoring System (CGMS) in Real Time", IEEE Transactions on Information Technology in Biomedicine, Mar. 2003, vol. 7, No. 1, pp. 43-53.

Steil et al., "Modeling Beta-Cell Insulin Secretion—Implications for Closed-Loop Glucose Homeostasis", Diabetes Technology and Therapeutics, 2003, vol. 5, No. 6, pp. 953-964.

Federiuk et al., "Induction of Type-1 Diabetes Mellitus in Laboratory Rats by Use of Alloxan: Route of Administration, Pitfalls, and Insulin Treatment, Comparative Medicine", 2004, vol. 54, No. 3, pp. 252-257.

Hovorka et al., "Closing the Loop: The Adicol Experience",. Diabetes Technology and Therapeutics, Jun. 2004, vol. 6, No. 3, pp. 307-318.

Steil et al., "Closed-Loop Insulin Delivery—The Path to Physiological Glucose Control", Advanced Drug Delivery Reviews, 2004, vol. 56, pp. 125-144.

Bequette, Wayne, "A Critical Assessment of Algorithms and Challenges in the Development of a Closed-Loop Artificial Pancreas", Diabetes Technology and Therapeutics, 2005, vol. 7, No. 1, pp. 28-47.

\* cited by examiner

STABILIZED GLUCAGON SOLUTIONS AND USES THEREFOR

CROSS-REFERENCE TO PRIORITY APPLICATION

This application is based upon and claims the benefit under 35 U.S.C. §119(e) of U.S. Provisional Patent Application Ser. No. 61/354,457, filed Jun. 14, 2010, which is incorporated herein by reference in its entirety for all purposes.

CROSS-REFERENCE TO OTHER PATENT DOCUMENTS

The following patent documents are incorporated by reference in their entireties for all purposes: U.S. Pat. No. 5,711,861; U.S. Pat. No. 6,212,416; U.S. Pat. No. 6,466,810; U.S. Pat. No. 7,433,727; and U.S. Patent Application Publication No. 2008/0027301.

INTRODUCTION

Glucose levels in the blood are regulated by peptide hormones produced by the pancreas. Pancreatic beta cells secrete insulin when blood glucose is high, such as after a meal, to promote glucose uptake by tissue. For example, insulin stimulates the liver to take up glucose for conversion to glycogen for storage. In contrast, alpha cells of the pancreas secrete glucagon when blood glucose is low, to induce the liver to break down glycogen into glucose. The glucose is released into the blood to elevate blood glucose.

The metabolic disease diabetes mellitus results when glucose regulation is defective, producing chronically high levels of glucose in the blood. Chronic high blood sugar can cause various health complications, such as damage to tissue (e.g., kidney, cardiovascular, retinal, neurological, etc.). Diabetes can result when the body does not generate sufficient insulin (Type 1 diabetes) or is resistant to the presence of insulin (Type 2 diabetes), among others. Both types of diabetes may be treated with insulin injections.

One of the problems associated with injection of insulin is overshoot, where blood glucose falls below the normal range to produce hypoglycemia. Since the brain is dependent on glucose for energy, hypoglycemia impairs brain function. Mild-to-moderate hypoglycemia can be self-diagnosed and quickly self-treated by orally ingesting a source of glucose or other sugar, such as a candy bar or a soft drink. However, severe hypoglycemia can render a diabetic person unconscious and in need of first aid treatment. To rescue the diabetic person, an emergency injection of glucagon is commonly utilized to elevate blood glucose to a safe range. The glucagon can be injected intramuscularly, intravenously, or subcutaneously to rapidly increase blood glucose. Without a timely glucagon injection, permanent brain damage or death can ensue.

Injectable glucagon formulations are available commercially. However, the glucagon is not provided in solution. Instead, the glucagon is present in a powdered form that must be reconstituted with a sterile diluent immediately prior to injection. This reconstitution step is undesirable because it delays injection and may introduce errors, such as incomplete glucagon solubilization, incorrect diluent volume, addition of a nonsterile diluent, and the like.

Glucagon reconstitution is required for these formulations because the glucagon is not stable in solution. Monomers of glucagon can rapidly associate with one another to form aggregates, such as amyloid fibrils, precipitates, gels, and the like. The aggregates may have less activity and/or delayed activity. More significantly, the aggregates may be toxic or may cause disease. In particular, amyloid fibrils composed of various proteins have been associated with diseases such as Alzheimer's disease, Huntington's disease, rheumatoid arthritis, and atherosclerosis, among others. Perhaps for this reason, the FDA-approved instructions for commercially-available glucagon allow only for immediate usage of glucagon after the powder is reconstituted in aqueous solution.

Glucagon has an isoelectric point of about 7. As a result, the peptide tends to be insufficiently soluble near a neutral pH. To improve solubility, commercial preparations rely on an acidic pH of about 3. However, fibril formation of glucagon is generally quite rapid at this low pH.

Glucagon also may be used in a drug delivery device that functions as an artificial pancreas. The device may utilize both an insulin pump and a glucagon pump containing solutions of insulin and glucagon, to respectively lower and raise blood glucose levels. The device monitors blood glucose levels in a diabetic subject and operates with closed loop control to maintain the glucose level within an acceptable range by infusing insulin and glucagon into the subject at appropriate rates and times. However, for the device to be feasible, the glucagon must be sufficiently stable to be stored near the subject's body in the glucagon pump for days (e.g., at least three days). Accordingly, commercial glucagon formulations available currently are not suitable for use by an artificial pancreas since these formulations cannot be stored in an aqueous form.

There remains a need for stabilized glucagon solutions.

SUMMARY

The present disclosure provides stabilized glucagon solutions, methods of storing and using the stabilized glucagon solutions, and drug delivery devices containing the stabilized glucagon solutions. In some embodiments, the glucagon solutions may be alkaline, such as with a pH of at least about 9. The glucagon solutions may be resistant to aggregation of glucagon when the solutions are stored for a prolonged period, such as at least about three days, at room temperature and/or physiological temperature.

DETAILED DESCRIPTION

The present disclosure provides stabilized glucagon solutions, methods of storing and using the stabilized glucagon solutions, and drug delivery systems and devices containing the stabilized glucagon solutions. In some embodiments, the glucagon solutions may be alkaline, such as with a pH of at least about 9. The glucagon solutions may be resistant to aggregation of glucagon when the solutions are stored for a prolonged period, such as at least about three days, at room temperature and/or physiological temperature.

A composition for treating a glucagon-responsive medical condition is provided. The composition may comprise a pharmaceutically-acceptable aqueous solution of glucagon. The solution may be alkaline, such as having a pH of greater than about 9. The glucagon may remain substantially non-aggregated when the solution is stored at a physiological temperature for at least three days.

A method of treating a glucagon-responsive medical condition is provided. In the method, an aqueous solution of glucagon at a pH of greater than about 9 may be provided. The solution may be stored in liquid form for at least three days at a physiological temperature without substantial aggregation of the glucagon. At least a portion of the solution may be delivered into a subject after the solution is stored.

A drug delivery system is provided. The system may comprise a container holding an aqueous solution of glucagon at a pH of greater than about 9. The glucagon may remain substantially non-aggregated when the solution is stored at physiological temperature for at least three days. The system also may comprise an outlet through which the solution is configured to be driven from the container for delivery into a subject.

Further aspects of the present disclosure are described in the following sections: (I) definitions, (II) overview of stabilized glucagon solutions, and (III) examples.

I. DEFINITIONS

Technical terms used in this disclosure have the meanings that are commonly recognized by those skilled in the art. However, the following terms may have additional meanings, as described below.

Subject—a recipient of a drug such as glucagon.

Drug delivery device—an appliance for delivering a drug, such as glucagon. The appliance may be configured to deliver the drug through any suitable route, such as parenteral or enteric (e.g., orally), among others. If parenteral, the appliance may deliver the drug by injection (e.g., by injection that is intraarterial, intravenous, intramuscular, intradermal, subcutaneous, etc.), intranasally, inhalationally, transdermally, etc. Injection may be as a bolus or by infusion, among others. Exemplary drug delivery devices includes pumps, syringes, injection pens, patches, needle-less injectors, and the like.

Pharmaceutically acceptable—approved by a regulatory agency of a federal or state government or listed in the U.S. Pharmacopeia or other generally recognized pharmacopeia for use in animals, and more particularly, in humans.

Stable—resistant to aggregation that forms substantially larger structures from monomeric glucagon, such as fibrils, a precipitate, a gel, visible cloudiness, or any combination thereof, among others. A glucagon solution that is resistant to aggregation does not exhibit substantial glucagon aggregation (i.e., remains substantially non-aggregated) when stored for at least a specified period of time and at or above a specified temperature or temperature range. Substantial glucagon aggregation is achieved when at least about 25% or 10% of the glucagon is aggregated.

Alkaline—a pH of greater than 7. Exemplary alkaline solutions of glucagon have a pH of greater than about 8 or 9, about 9.5 to 10.5, or about 10, among others.

Glucagon—a glucose-increasing peptide that is identical or similar to native glucagon. Native glucagon is composed of 29 amino acids, has a molecular weight of 3485 daltons, and is fully conserved in all or nearly all mammals. The glucagon may be an analog of native glucagon, differing from the native form by one or more amino acid substitutions, additions, and/or deletions. Alternatively, or in addition, the glucagon may be a derivative of native glucagon that includes one or more chemical modifications of one or more amino acids. Exemplary chemical modifications include acetylation, methylation, amidation, decarboxylation, phosphorylation, disulfide cross-linking, glycosylation, farnesylation, etc.

Physiological temperature—a temperature of about 30 to 37 degrees Celsius.

Room temperature—a temperature of about 20 to 25 degrees Celsius.

II. OVERVIEW OF STABILIZED GLUCAGON SOLUTIONS

Figure 1:
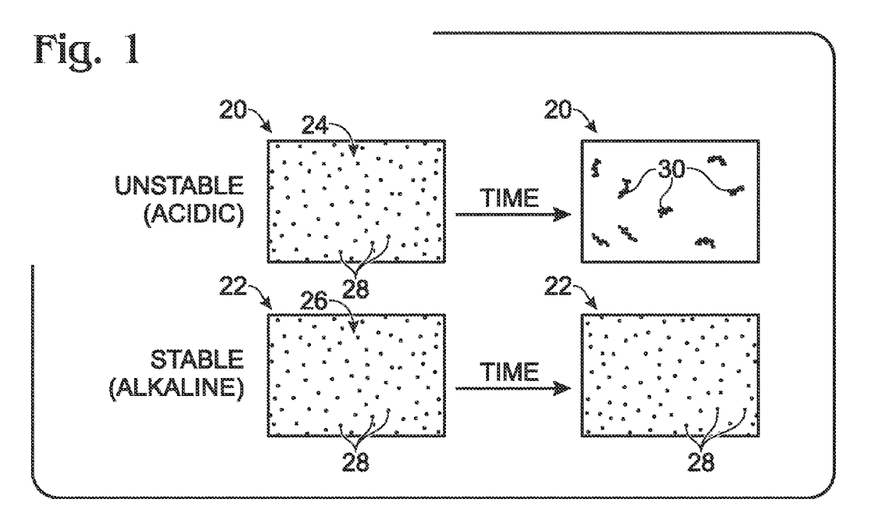
FIG. 1 is a schematic view of an unstable, acidic glucagon solution (top row) and a stable, alkaline glucagon solution (bottom row) being aged and illustrating aggregation of glucagon monomers in the acidic solution while the monomeric form is preserved in the alkaline solution, in accordance with aspects of the present disclosure.

FIG. 1 shows a schematic view of a pair of containers 20, 22 holding respective glucagon solutions 24, 26 that are unstable (top row) and stable (bottom row).

First glucagon solution 24 is an acidic aqueous solution, such as a commercially available glucagon solution at pH 3.0. When placed into solution, the glucagon aggregates over time, to convert glucagon monomers 28 (on the left) to aggregated glucagon (on the right), such as amyloid fibrils 30. The rate of glucagon aggregation may be dependent upon the temperature at which the glucagon solution is stored (also termed "aged"), with a higher temperature generally producing more rapid aggregation.

Second glucagon solution 26 is an alkaline aqueous solution. The alkaline pH of solution 26 stabilizes the solution against aggregation of glucagon monomers 28. Accordingly, when incubated for a time period and at a temperature sufficient to cause substantial aggregation of glucagon in acidic solution 24, alkaline solution 26 is stable, with the glucagon remaining substantially non-aggregated.

The glucagon may be present at any suitable concentration in alkaline solution 26. In exemplary embodiments, the glucagon is present at a concentration of about 0.1 to 10 mg/mL, 0.5 to 5 mg/mL, 0.5 to 1.5 mg/mL, or about 1 mg/mL, among others.

Alkaline solution 26 may be stable for any suitable storage period and at any suitable storage temperature. For example, the solution may be stable when stored for at least about 1, 2, 3, 5, 7, 14, 21, or 28 days at a temperature of at least about 20, 25, 30, or 37° C.

The alkaline solution may contain a buffering agent, salt, a surfactant, a sugar, a stabilizer, a preservative, or any combination thereof, among others. In some cases, the solution may contain substantially no surfactant.

The buffering agent may include an ampholyte, that is, a substance that can act as an acid or a base. Exemplary ampholytes include an amino acid (e.g., glycine, alanine, leucine, asparagine, histidine, glutamic acid, etc.), a diamino acid (e.g., glycylglycine, glycylalanine, etc.), or the like.

The alkaline solution may have any suitable osmolarity. For example, the osmolarity may be about 200-500 or 250-400 mOsm, among others.

Figure 2:
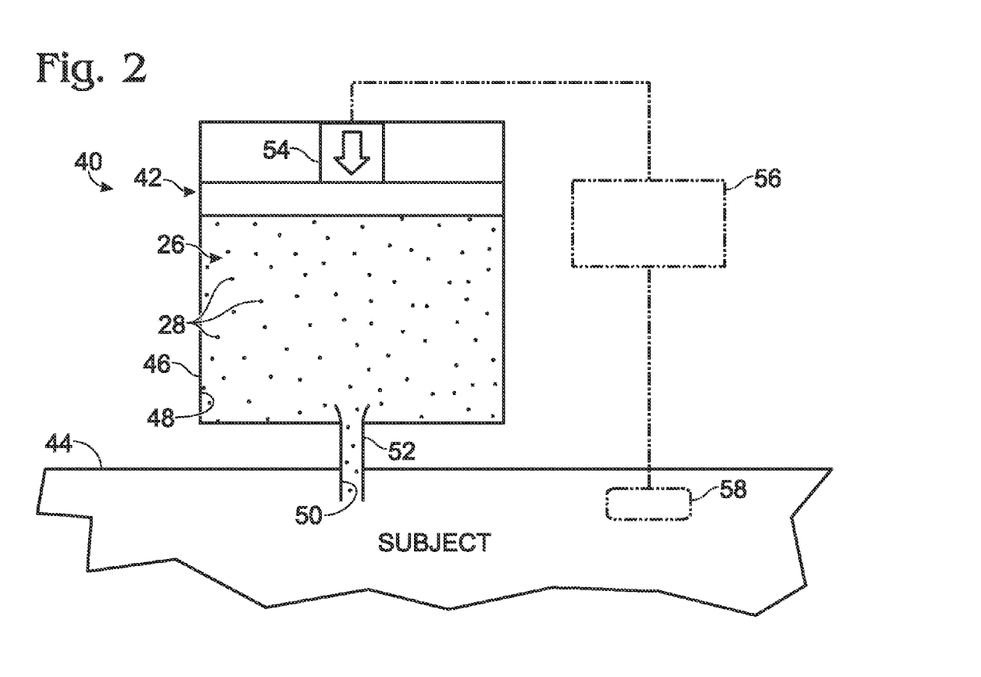
FIG. 2 is a schematic view of an exemplary drug delivery device pumping an aged, stable glucagon solution into a subject, in accordance with aspects of the present disclosure.

FIG. 2 shows an exemplary drug delivery device 40, including a pump 42, delivering a portion of alkaline solution 26 into a subject 44. Solution 26 has been stored in the device for at least a day at physiological temperature but remains substantially non-aggregated.

Drug delivery device 40 may include at least one container 46 to hold solution 26. The container may form a chamber 48 of the pump. In any event, the container may be sealed to prevent contamination and/or evaporation of solution 26.

Drug delivery device 40 also may include at least one outlet or port 50 through which solution 26 may exit the device for delivery to the subject 44. The outlet may be formed by a tube 52 (e.g., a needle), among others. The outlet may be connected or connectable to chamber 48 for fluid communication therebetween. Outlet 50 may carry and/or emit solution 26 into and/or onto the subject. Delivery into the subject may be by injection through the skin (e.g., intravenous, intramuscular, or subcutaneous injection). Delivery onto the subject may include dermal application.

The drug delivery device may include a pressure source 54 that drives fluid from container 46 through outlet 50. The pressure source may include a motor, one or more piezoelectric elements, one or more heater elements, a compressed fluid, or the like.

Device 40 may provide closed loop control of glucagon delivery. The device may be equipped with a processor 56 and at least one glucose sensor 58 in communication with the processor. The processor may control operation of pressure source 54, such as the timing and rate at which the pressure source drives fluid through outlet 50.

The glucose sensor may be positioned to monitor a glucose concentration of the subject. For example, the glucose sensor may be implanted in the subject or disposed on or adjacent the subject's skin, among others.

Device 40 may be utilized to perform a method of regulating blood glucose and/or of treating hypoglycemia. At least one glucose sensor may be utilized to monitor a concentration of glucose in a subject. The sensor may generate a sensor output signal based on the monitored concentration. The output signal may be used to generate an input signal from the sensor. The input signal may be processed by a processor using an algorithm to generate a processor output signal for controlling the pressure source. The algorithm may be a proportional and/or derivative algorithm, and, in some cases, a fading memory proportional derivative algorithm. Glucagon may be delivered based on the input signal from the sensor, that is, based on a proportional error of glucose concentration and/or a derivative error of glucose concentration. For example, glucagon may be delivered when the glucose concentration is falling.

Further aspects of drug delivery devices and methods of delivering glucagon are disclosed in the patent documents listed above under Cross-References, which are incorporated herein by reference, particularly U.S. Patent Application Publication No. 2008/0027301.

III. EXAMPLES

The following examples describe selected aspects of exemplary systems for formulating, testing, and utilizing stable aqueous glucagon solutions. These examples are intended for illustration and should not be interpreted as limiting the entire scope of the present disclosure.

A. STUDY OVERVIEW

The following experiments investigate whether aging at different pH values and solvents would reduce cytotoxicity in fibroblast cell culture and the tendency toward amyloid formation. The alkaline range was studied in addition to the acidic range. Since glucagon is minimally soluble, the neutral range may not be suitable for storage after aqueous reconstitution.

To avoid misattribution of toxicity to glucagon per se, the specific effects of pH and osmolarity on cytotoxicity in the fibroblasts were investigated, especially because earlier studies did not adequately address these issues.

The experiments also address the bioactivity of amyloid-rich, aged glucagon solutions in nondiabetic pigs, since earlier data suggested that aged solutions might have greater bioactivity than might be expected. To understand the pharmacokinetic effects of aged glucagon in these animals, periodic serum samples were collected for measurement of glucagon.

B. MATERIALS AND METHODS

1. Cytotoxicity Measurements in Cell Culture

Studies assessing the potential cytotoxic effects of native glucagon employed NIH 3T3 cells cultured in Dulbecco's modified Eagle's medium (DMEM) (Invitrogen, Carlsbad, Calif.) and 10% fetal bovine serum (FBS) (Invitrogen) in a 37° C. incubator set at 5% $CO_2$ and 95% humidity. Cytotoxicity was examined after cultured cells were exposed to native glucagon, which was either freshly prepared or aged in aqueous solution for varying lengths of time at different concentrations. Two types of native glucagon preparations were studied: a lactose-rich commercial preparation of glucagon hydrochloric acid (HCl) (GlucaGen®, Novo Nordisk NS, Princeton, N.J.) and a lactose-free glucagon preparation (described later).

2. Study of Commercially-Available Lactose-Rich Glucagon

Twenty-four hours prior to glucagon exposure, cells were seeded at approximately $1-2\times10^4$ cells per well in 96-well plates (Corning Inc., Lowell, Mass.) with DMEM, which was supplemented with 10% FBS and 2 µM insulin. Immediately prior to glucagon exposure, the media was replaced with serum-free DMEM. The glucagon HCl mixture (GlucaGen) was received freeze-dried and was a generous gift from Novo Nordisk NS. GlucaGen is enriched with lactose, and when reconstituted with water to the FDA-approved concentration of 1 mg/mL, is designed to yield a pH of approximately 3.

The GlucaGen mixture was reconstituted with sterile water in order to create concentrations of 5.0 mg/mL, 1.0 mg/mL, 0.5 mg/mL, 0.3 mg/mL, and 0.1 mg/mL. All concentrations were allowed to age for 0, 1, 2, and 7 days in a tissue culture incubator. NIH 3T3 cells were then treated with each aged glucagon preparation for 24 hours before cytotoxicity tests were carried out. Each glucagon preparation was added to the wells as a 1:1 ratio of glucagon and DMEM. In addition, the commercial 1.0 mg/mL preparation of GlucaGen was assayed for amyloid with Congo red immediately after reconstitution and after 4 hours, 1 day, 3 days, and 5 days of aging at 37° C. A description of the Congo red procedure is given below. This reconstitution was carried out in sterile water according to the manufacturer's instructions.

A cell lysis solution composed of acetic acid and ethanol was used as the positive control for cytotoxicity and DMEM alone was the negative control. Lactate dehydrogenase (LDH) release was used to measure cell death (Roche Cell Death Kit, Roche Applied Science, Inc., Indianapolis, Ind.). In this assay, 120 µL of the reaction mixture (a mixture of diaphorase/nicotinic acid dinucleotide, iodotetrazolium chloride, and sodium lactate) was placed into each well. The plate was then incubated for 30 minutes at room temperature away from direct light. Absorbance at 492 nm with a reference wavelength of 690 nm was measured using a SpectraMax M5 spectrophotometer (Molecular Devices Inc., Sunnyvale, Calif.).

For some studies, cell viability was measuring using Cell Proliferation Reagent WST-1 (Roche Applied Science, Inc., Indianapolis, Ind.), which is based upon the cleavage of water-soluble tetrazolium-1 (WST-1) to formazan. After cells were exposed to a 1:1 ratio of glucagon and DMEM for 24 hours, 12 µL of WST-1 reagent was added to each well. The plate was then incubated for 3 hours in a 37° C. incubator at 5% $CO_2$ and 95% humidity, and absorbance was then measured as described earlier at 450 nm with a reference wavelength of 690 nm.

3. Studies of Lactose-Free Glucagon

Twenty-four hours prior to glucagon exposure, cells were seeded at approximately $1-2\times10^4$ cells/well in 96-well plates in DMEM supplemented with 10% FBS and 2 µM insulin. Immediately prior to glucagon exposure, all media was replaced with serum-free DMEM. Lyophilized synthetic glucagon (Sigma-Aldrich Product #G2044, St. Louis, Mo.) was used as a source of native glucagon.

Native glucagon was reconstituted with sterile phosphate-buffered saline (PBS), pH 7.4; 20 mM Tris buffer, pH 8.5; and 20 mM glycine buffer, pH 10. After buffer solutions were prepared and adjusted to specific pH levels, they were filtered through a 0.22 µm sterile Millipore™ syringe (Millipore Corp., Billerica, Mass.) before use. Three concentrations of glucagon were prepared: 2.5 mg/mL, 1.0 mg/mL, and 0.3 mg/mL. All concentrations were allowed to age for 0, 3, and 5 days in a tissue culture incubator. The NIH 3T3 cells were then treated with each aged glucagon preparation for 24 hours before cytotoxicity tests were carried out.

After glucagon was added to DMEM, the resulting pH value for the GlucaGen (at an original concentration of 5 mg/mL) was 6.55 and for the original concentration of 1 mg/mL was 7.49. For the lactose-free glucagon (2.5 mg/mL original concentration), the resulting pH was 8.15 for Tris and 8.84 for glycine.

To avoid hypotonicity of the glucagon-DMEM solutions, the DMEM was supplemented with sodium chloride (NaCl) for the Tris and glycine solutions, so that the final osmolarity fell in the range of 320-350 mOsm/kg. Native glucagon was insoluble (yielding a precipitate) in PBS, and, for this reason, cytotoxicity results are not reported for PBS-buffered glucagon.

4. pH Study

A pH study was carried out to assess the direct effect of pH on cytotoxicity in NIH 3T3 cells. Serum-free DMEM was used as the test solution. The pH of the DMEM was adjusted using HCl and sodium hydroxide (both from Sigma-Aldrich, St. Louis, Mo.). In order to assess cytotoxicity, pH values of 10.0, 8.5, 7.6, 6.5, 5.0, 4.0, and 3.0 were used. All pH solutions were prepared the day of use. Twenty-four hours prior to exposure to the pH treatments, cells were seeded at approximately $1-2\times10^4$ cells/well in 96-well plates with DMEM supplemented with 10% FBS and 2 µM insulin. Immediately prior to exposure to the various pH solutions, all media was removed from the cells. The pH treatments were then added to the cells and incubated at 37° C. for 24 hours. The WST-1 assay was used to assess cytotoxicity and viability.

5. Osmolarity Study

In order to determine effects of osmolarity on cell viability, osmolarities of 85, 170, 340, 685, 855, and 1030 mOsm were tested. The lower osmolarities of 85 and 170 mOsm were obtained by dilution of serum-free stock DMEM (Invitrogen) with sterile water. The osmolarity of 340 mOsm was obtained by using this same stock DMEM (340 mOsm, as reported by the manufacturer's Certificate of Analysis) without dilution with sterile water or supplementation with NaCl. The higher osmolarities of 685, 855, and 1030 mOsm were obtained by supplementing the stock DMEM with NaCl.

Twenty-four hours prior to exposure of osmolarity treatments, cells were seeded at approximately $1-2\times10^4$ cells/well in 96-well plates with DMEM supplemented with 10% FBS and 2 µM insulin. Immediately prior to the exposure of varying osmolarities, all media was removed from the cells. The osmolarity treatments were then added to the cells for 24 hours. The WST-1 assay was used to assess cell viability, as described earlier.

6. Condo Red Binding Assay

Glucagon aggregates that reacted with Congo red were studied using a protocol modified from Klunk and colleagues. A solution of Congo red (Sigma-Aldrich, St. Louis, Mo.) was prepared by adding 5 µL of 25 µM Congo red to 1 mL of 20 mM potassium phosphate buffered to pH 7.4. This solution was filtered through a 0.22-µm filter. Ten µL of each glucagon preparation (each aged at 37° C. at 1 mg/mL) were added to this Congo red solution. To confirm that the Congo red staining procedure would not be impaired by assaying an alkaline sample, we verified that adding the highly alkaline glycine (pH 10) sample to the buffered salt solution with Congo red did not change that solution's pH.

When fibrillation occurred, a small gel-like precipitate stained with Congo red was typically found without a diffuse change in the color of the solution. Accordingly, there were very inconsistent readings with the spectrophotometer. For this reason, a visual test by a researcher who was unaware of the study conditions was used for data analysis. More specifically, the intensity of bound Congo red was scored by a visual test based on a scale of 0 to 6, according to the size and intensity of the red-colored gel. Before this visual test was conducted, a number of the samples were shown separately to others. A very high degree of concordance was observed.

7. Solubility Study

A solubility study for native glucagon was carried out at alkaline pH levels prior to the 5-day glucagon aging study. It is already known that glucagon is highly soluble at an acidic pH, so solubility in the acid range was not studied. For glucagon dissolved in Tris at pH 8.5 and the glucagon dissolved in glycine at pH 10, various concentrations were prepared in 96-well plates at 37° C. and their absorbance was measured at 280 nm. The absorbance at 280 nm increases linearly as the concentration of soluble protein increases, but when the soluble concentration is exceeded, the absorbance plateaus. We found that at pH values of 8.5 and 10, when the concentration of glucagon was raised to approximately 3 mg/mL or higher, the absorbance response no longer rose in a linear fashion, demonstrating reduced solubility. For this reason, at alkaline pH, the highest concentration used in these studies was 2.5 mg/mL.

8. Size-Exclusion Chromatography (SEC)

Glucagon (native) was purchased from Sigma-Aldrich (St. Louis, Mo.). The glucagon was dissolved and aged for 21 days at 37° C. in three buffers: citrate buffer (pH 3.0), Tris (pH 8.5), and glycine (pH 10.0), all at 1 mg/mL concentrations. Buffer solutions were filtered through a 0.22-μm, sterile Millipore syringe before use. Samples of fresh and aged glucagon were fractionated on a Tosoh TSK-Gel 4000SWxl column (Tosoh Bioscience LLC, Montgomeryville, Pa.) at ambient temperature using an Agilent 1100 HPLC system (Agilent Technologies, Inc., Santa Clara, Calif.). Each preparation was studied using a citrate mobile phase (20 mM citrate buffer containing 130 mM NaCl, pH 3.0). The glucagon aged in glycine was also studied using a mobile phase of PBS (Invitrogen) at pH 7.4. The peptides were eluted under constant flow at 0.7 mL/min and the absorbance monitored at 214 nm (peptide bond) and 280 nm (aromatic ring). The column was calibrated with blue dextran (2,000,000 Da) and a series of protein standards of varying molecular weight including, thyroglobulin (690,000 Da), glucose oxidase (160,000 Da), bovine serum albumin (66,500 Da), porcine insulin (5777 Da), glucagon (3482 Da), and buserelin (1239 Da). The outcome metric was the area under the absorbance curve (280 nm) for the peak that eluted at 19.5 minutes (i.e., the glucagon monomer peak, 3.5 kDa).

9. Glucagon Administration in Pigs

Studies that involved animals followed the United States National Institute of Health guidelines for the use and care of laboratory animals. In addition, the Legacy Institutional Animal Care and Use committee gave written approval for the study before it was carried out. The purpose of the pig study was to collect blood for analysis of glucagon plasma levels. GlucaGen was reconstituted with sterile water as per the manufacturer's instructions to a concentration of 1 mg/mL.

Prior to addition of blood to serum collection tubes for later glucagon assay, 1000 KIU of aprotinin solution per milliliter of whole blood were added to each tube as a proteolysis inhibitor.

Young Yorkshire farm pigs (25-40 kg) were used for this study. Pigs were not fed on the morning of the study. A pig was sedated with Telazol and weighed. The animal then underwent tracheal intubation. For anesthesia, the pig was maintained on 1.5-2% isoflurane with oxygen. A SC dose of octreotide acetate (44 μg/kg) was given to block endogenous secretion of insulin and glucagon. An 18-gauge catheter was placed in the ear vein and normal saline was given slowly to keep the vein open. A heating pad was placed over the catheter to arterialize the venous blood. When vital signs were stable, the study was initiated.

Every 15 minutes throughout the study, 0.1 mL of blood was drawn from the intravenous catheter for measurement of blood glucose using a Hemocue 201 glucose analyzer (Hemocue Inc., Lake Forest, Calif.). At intervals, blood was obtained for later measurement of glucagon immunoreactivity (radioimmunoassay) in serum.

Thirty minutes after giving the octreotide, a SC dose of glucagon (either a low dose of 1 μg/kg (n=2 for fresh glucagon and n=2 for aged glucagon) or a maximal dose of 1 mg (n=1 for fresh and n=1 for aged) was given subcutaneously. A second dose of octreotide acetate (same dose as first) was administered 2 hours after the first dose. When the blood glucose returned to fasting or near-fasting levels, the study was terminated. The pig was observed during emergence from anesthesia until it could stand unassisted.

10. Statistics

Student's t-test with the Bonferroni adjustment was used for comparisons (paired or unpaired, as appropriate). Before the adjustment, the starting alpha was 0.05. Thus, for the study of cytotoxicity of GlucaGen, there were five concentrations and four study durations, yielding a final alpha of 0.05/20=0.0025. Similarly, for the study of lactose-free glucagon, there were two types of glucagon, three concentrations, two storage pH levels, and two durations, yielding a final alpha of 0.05/24=0.0021.

C. RESULTS

Congo red studies were carried out on GlucaGen reconstituted at 1 mg/mL. The Congo red assay was carried out in triplicate on this lactose-rich preparation immediately after reconstitution and after being aged at 37° C. for various lengths of time. Using a scale of 0-6, with a score of 6 being maximal, Congo red scores of 0 were observed with no aging, 0 after 4 hours of aging, 1.5 after 24 hours of aging, 3.75 after 3 days of aging, and 6 after 5 days of aging (data not shown).

Figure 3:
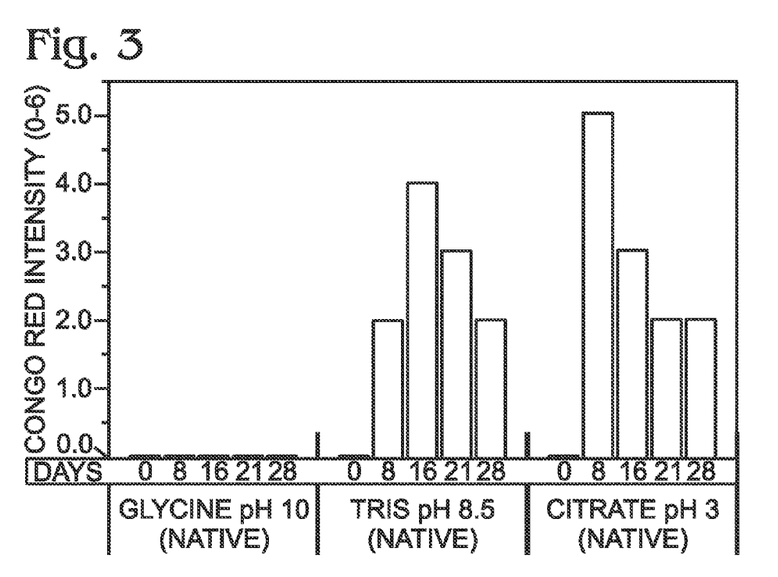
FIG. 3 is a graph of results of a Congo red assay for glucagon preparations aged at 37° C. for varying lengths of time, in accordance with aspects of the present disclosure.

FIG. 3 shows results from a series of Congo red assays performed on lactose-free preparations of native glucagon aged for longer periods of time. There was no Congo red binding at day 0 (freshly prepared, without aging) under any condition. Beginning at day 8, Congo red amyloid intensity was greatest in citrate buffer at pH 3. At a mildly alkaline pH of 8.5, there was substantial Congo red intensity at day 8 with the native glucagon. At a pH of 10, there was no Congo red staining for native glucagon, even after 28 days.

Figure 4:
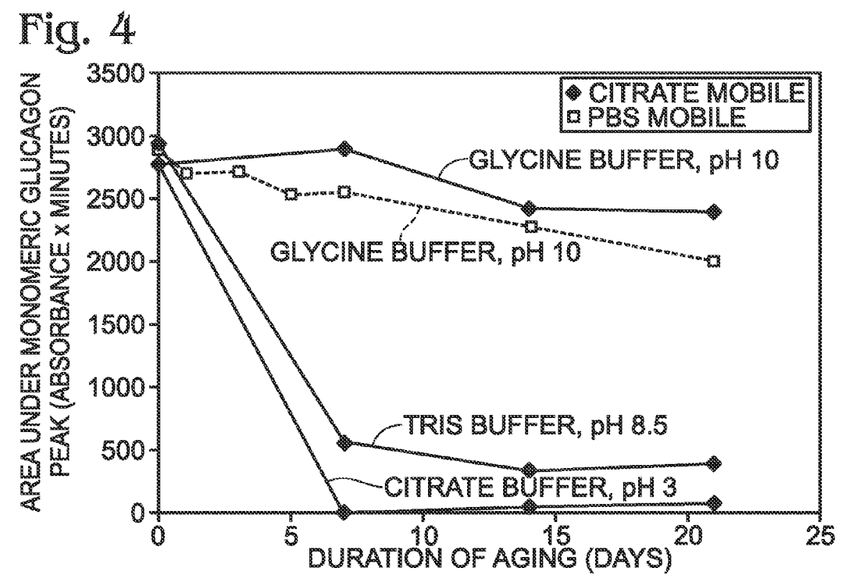
FIG. 4 is a graph of size exclusion chromatography (SEC) carried out on fresh and aged preparations of native glucagon, in accordance with aspects of the present disclosure.

FIG. 4 shows a graph of results from size exclusion chromatography performed on native preparations of glucagon. Shown here are the areas under the curve (units are absorbance×minutes) for the main monomeric glucagon peak (molecular weight 3.5 kDa) obtained at different periods of aging at 37° C. up to 21 days for glucagon aged in glycine (pH 10), Tris (pH 8.5), and citrate (pH 3). All preparations were studied using a citrate mobile phase. The glycine preparation was also studied using a PBS mobile phase. Irrespective of the mobile phase, the glucagon dissolved in glycine (pH 10) demonstrated the greatest preservation of the monomeric glucagon peak over time.

When glucagon was aged in citrate at pH 3, the size of the glucagon monomeric peak declined rapidly and was absent after 7 days. When aged in Tris at pH 8.5, there was also a substantial loss of the glucagon peak. In contrast, when aged in glycine at pH 10, there was very little loss of the monomeric peak at 7 days, although modest loss occurred after 14 and 21 days. There was no obvious difference in the results for the glycine preparation when a mobile phase of PBS (pH 7.4) was used versus a mobile phase of citrate (pH 3).

Although the monomeric glucagon peak and the peaks from the various protein standards were always well-delineated, there were little if any large molecular weight peaks that would have indicated amyloid aggregates, even in preparations that lost the glucagon peak and were shown by other techniques to be rich in amyloid. This finding may be due to the fact that when the aging solution showed both solids (gels) and liquid, the very narrow gauge pipette tip used to acquire the sample tended to serve as a screen, allowed acquisition only of the nongelled liquid.

Figure 5:
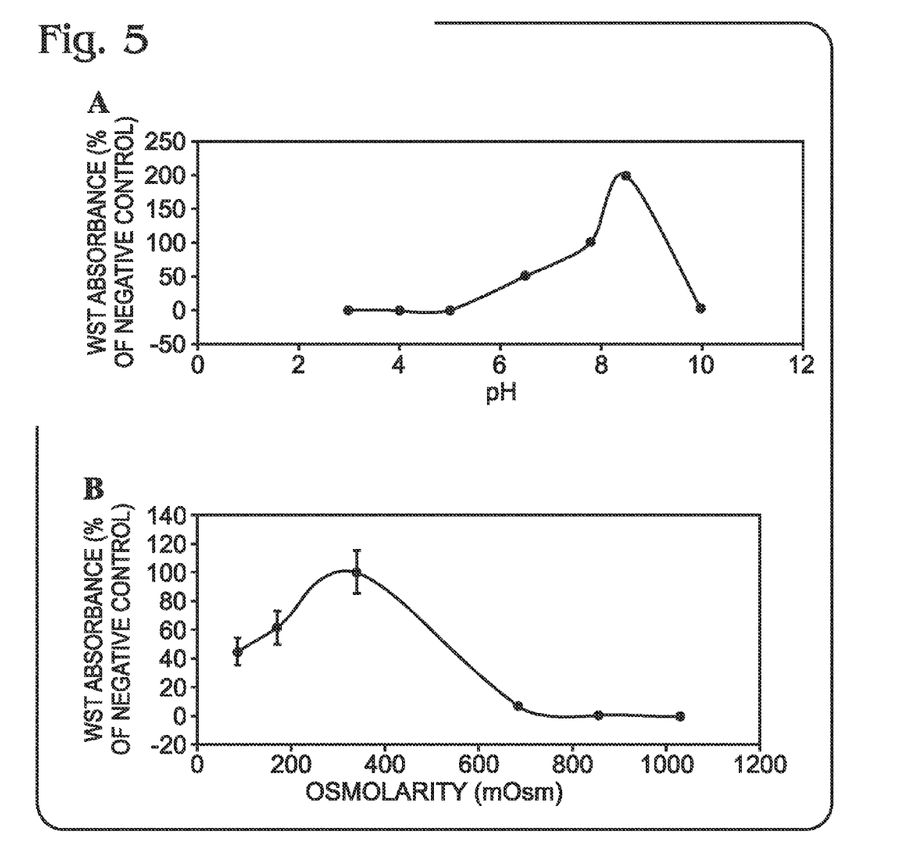
FIG. 5 is a pair of graphs of the effect of (A) pH and (B) osmolarity on cytotoxicity of NIH 3T3 fibroblasts in culture, using an WST-1 cell viability assay, in accordance with aspects of the present disclosure.

FIG. 5 shows a pair of graphs of the effect of (A) pH and (B) osmolarity on cytotoxicity of NIH 3T3 fibroblasts in culture, using a WST-1 cell viability assay. The ranges for pH and osmolarity that did not induce cytotoxicity, as measured by the WST-1 assay, were approximately 7.0-9.5 and 250-400, respectively.

The results of the LDH and WST-1 assays in initial experiments were concordant. However, owing to its better reproducibility during repeated measures for 5-7 days, subsequent cytotoxicity assays used the LDH assay.

Figure 6:
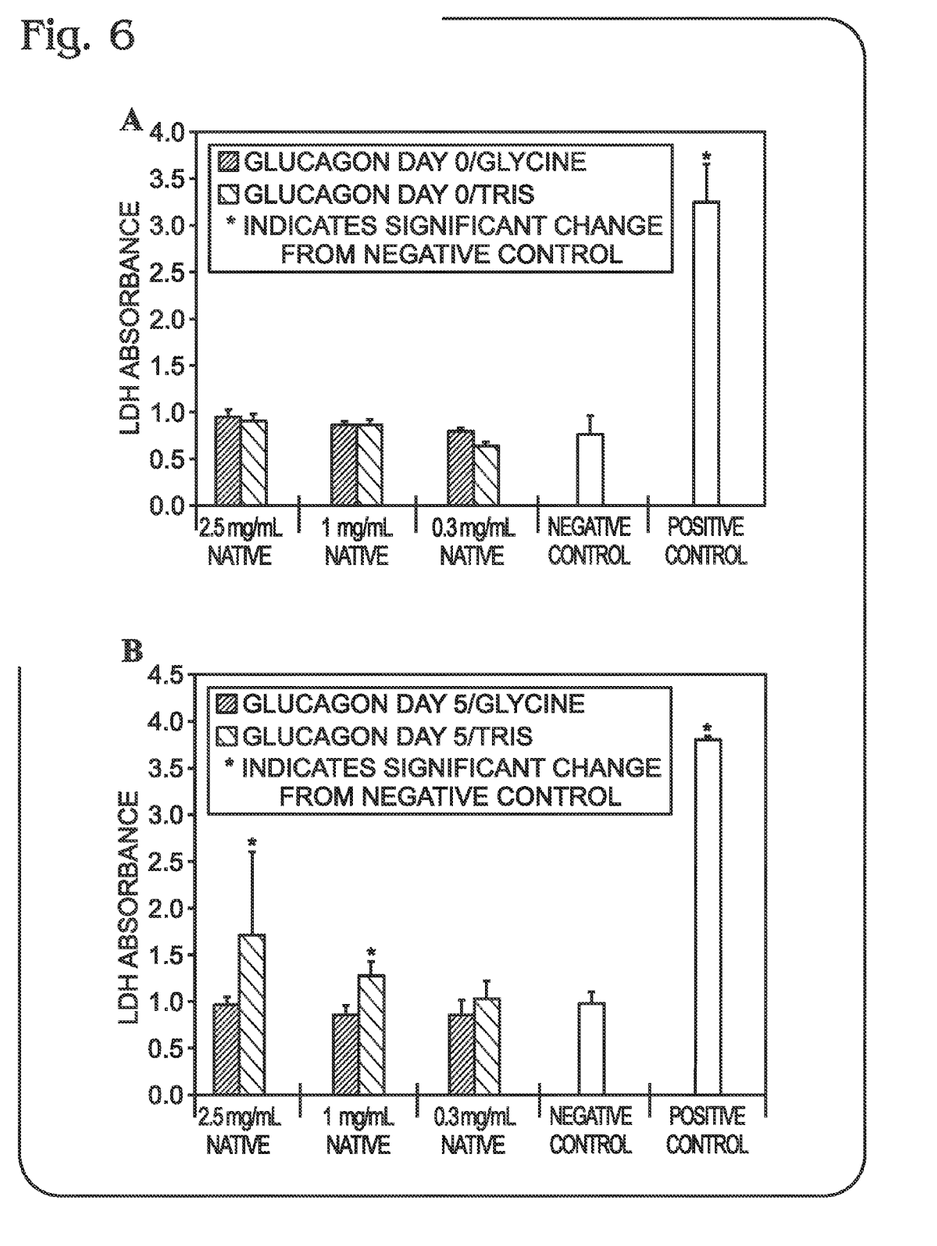
FIG. 6 is a pair of graphs of cytotoxicity results for lactose-free native glucagon at different concentrations with (A) no aging and (B) after aging for 5 days, in accordance with aspects of the present disclosure.

FIG. 6 shows cytotoxicity results for lactose-free glucagon at different concentrations with no aging (FIG. 6a) and after aging for 5 days (FIG. 6b). With no aging, there was no significant cytotoxicity at any concentration of the native hormone at either pH 8.5 or 10. After aging for 5 days, there was some evidence of toxicity at pH 8.5. At 5 days at a pH of 10 in glycine buffer, there was no evidence of cytotoxicity for either preparation.

Figure 7:
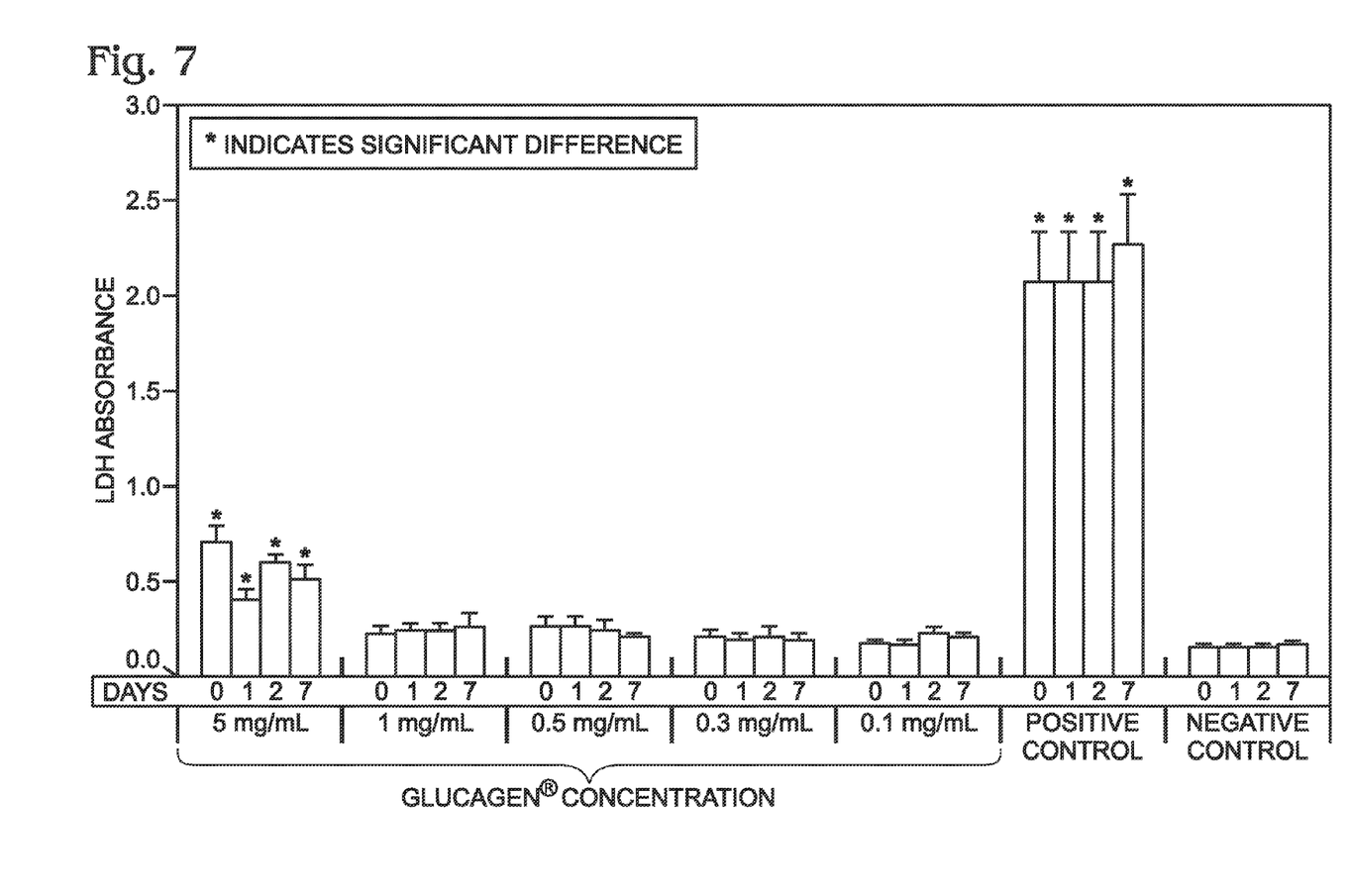
FIG. 7 is a graph of LDH assay results measured from NIH 3T3 fibroblasts exposed to a commercially available lactose-rich glucagon preparation (GlucaGen) aged for 0, 1, 2, and 7 days, in accordance with aspects of the present disclosure.

FIG. 7 shows LDH assay results for NIH 3T3 cells exposed to the commercially available lactose-rich glucagon preparation (GlucaGen) at pH 3 after aging for 0, 1, 2, and 7 days. Only the highest concentration (5 mg/mL) led to cytotoxicity, and it was clear that this toxicity was not related to the duration of aging. Indeed, the toxic effect of the highest concentration of glucagon was as prominent at day 0 as it was at day 7. Concentration of the lactose-rich glucagon mixture, not aging duration, was the relevant factor.

Figure 8:
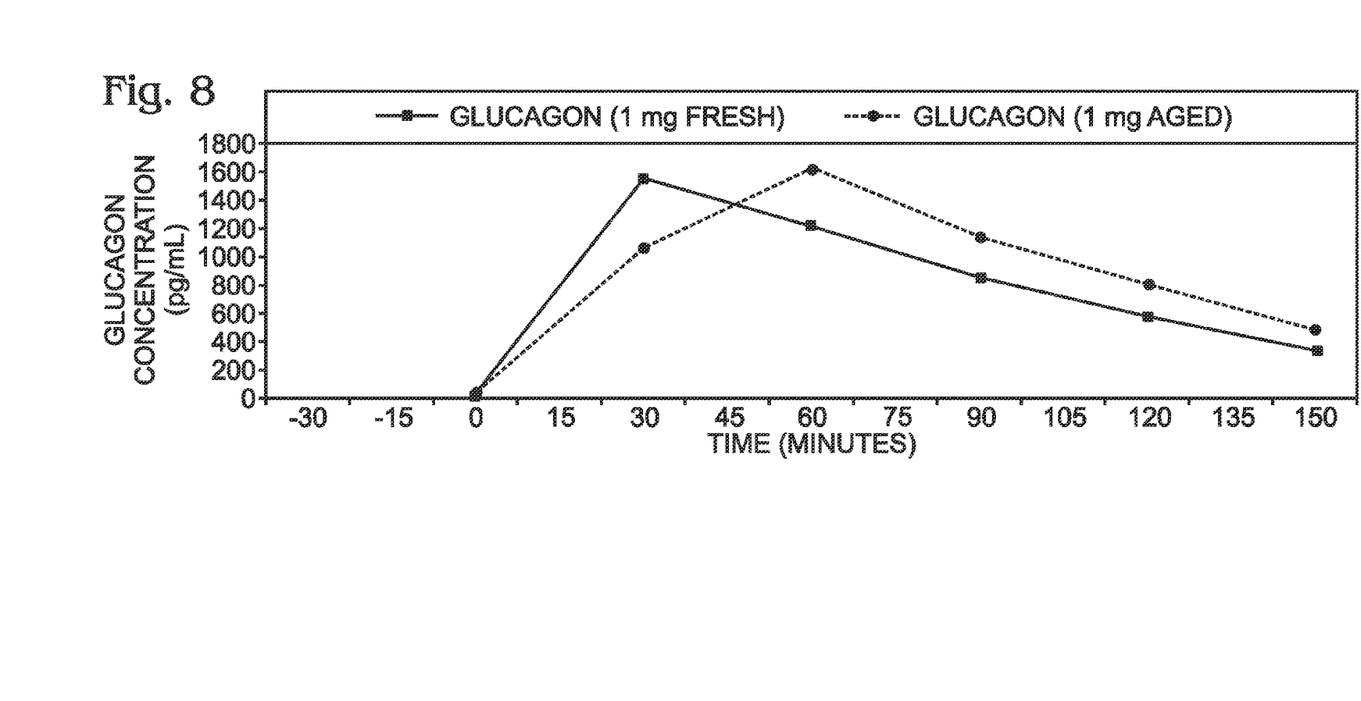
FIG. 8 is a graph of plasma levels of glucagon measured in a study in which fresh or aged glucagon (GlucaGen) was given to anesthetized pigs, in accordance with aspects of the present disclosure.

A pig study was performed in which fresh or aged (at 1 mg/mL) GlucaGen was given to anesthetized pigs. FIG. 8 shows the plasma levels of glucagon obtained. Although the maximal plasma levels were very similar for fresh versus aged glucagon, there was a tendency for the rise in glucagon to be slightly delayed in the aged preparation.

D. DISCUSSION

There is a need for glucagon to be sufficiently stable so that it can be indwelled in a portable pump for at least 3 days. The delivery apparatus and fresh aqueous glucagon could be loaded into the pump chamber at these intervals. It has been found that, in the setting of an artificial pancreas, glucagon delivered intermittently during declining incipient hypoglycemia usually protects against overt hypoglycemia in subjects with type 1 diabetes. These studies demonstrate the need for a stable aqueous preparation of glucagon. Currently, usage instructions for commercially available glucagon allow only for immediate usage of glucagon after the powder is reconstituted in aqueous solution. As is the case for many other proteins, glucagon has a tendency to form amyloid fibrils in aqueous solutions during aging. Onoue et al. asserted that aging of aqueous solutions of glucagon form amyloid fibrils that directly cause cytotoxicity, a conclusion similar to that of Maji and colleagues.

In experiments presented herein, it was found that under certain conditions, native glucagon is free of cytotoxicity even after aging in aqueous solution at body temperature for 5 days. No evidence was found for cytotoxicity from native glucagon at a pH of 10 in a glycine buffer up to maximally soluble concentrations of 2.5 mg/mL. A mild to moderate cytotoxicity was observed when the native glucagon was aged in Tris buffer at pH 8.5. It also was found that the maximally soluble concentration (5 mg/mL) of the commercial glucagon preparation (GlucaGen), whose pH after aqueous reconstitution is 3, caused marked cytotoxicity. It is important to note, however, that this toxicity was found at time zero, with no additional cytotoxicity after aging (discussed further later). Taking all the cytotoxicity results into consideration, including the present experiments addressing the pH effect, the alkaline pH range (e.g., a pH of 10) may be the safest option for avoiding cytotoxicity and amyloid fibril formation. It should be noted that the pH 10 preparation used, after dilution with the DMEM culture medium, yielded a pH of 8.8, a level that was only minimally toxic in the pH study.

With the same cell line used herein (NIH 3T3 fibroblasts) and the same assay for cytotoxicity (LDH), Onoue and colleagues reported that glucagon aged at a high concentration (5 mg/mL) caused definite cytotoxicity, even after aging for only 1 day. In that study, the preparation that was cytotoxic when aged was not cytotoxic with no aging. The reasons for the differing results of the present study and that of Onoue et al. are not perfectly clear, although there are several possibilities, including the conditions under which the cells were studied. First, the present study found substantial direct effects of pH and osmolarity on cytotoxicity with NIH 3T3 cells. The ranges of pH and osmolarity that showed acceptably low cytotoxicity were 7-9.5 and 250-400 mOsm, respectively. In the study of Onoue and colleagues, the concentration of HCl to which the glucagon was exposed was 0.01 M, which would result in a pH of approximately 2. Although it is true that when added to buffered cell media, the resulting pH could have been somewhat higher in their study, the resulting pH probably remained low and contributed to cell death. The osmolarity to which the cells were exposed during LDH testing was not provided in the Onoue study.

Given the effects of pH and osmolarity on cell viability, there are several possible causes of the present observation of cytotoxicity at high concentrations of the commercial glucagon preparation from Novo Nordisk: (1) the hyper-osmolarity of the solutions caused by the lactose in the high glucagon concentration study; (2) the low pH of the solutions; or (3) a direct toxic effect of amyloid fibrils. The finding of an immediate cytotoxic effect (with no aging) suggests that low pH or hyperosmolarity were the likely culprits, since the present study and others have found that the concentration and potential toxicity of amyloid fibrils increases with time. The high lactose concentration in the 5 mg/mL GlucaGen preparation (over 100 mg of lactose per mg of glucagon) was associated with a very high, nonphysiologic osmolarity of approximately 900 mOsm.

In the present study, there was an interest in aging glucagon at maximally soluble concentrations. It was found that the high concentration of 5 mg/mL examined in the acid pH experiments could not be achieved at higher pH levels. The maximal solubility of glucagon in the alkaline range with glucagon was 2.5-3.0. Pedersen et al. reported solubility data that was similar to the present study, i.e., maximal solubility at acid pH, very little solubility at neutral pH, and rising solubility as pH is raised above neutral.

The Congo red results presented herein show that formation of amyloid occurred quickly, with very high levels at 5-8 days when glucagon was aged in acid solutions, either with the commercial lactose-rich preparation or with the lactose-free preparation. In contrast, Congo red binding was much lower in alkaline preparations. At the highest pH of 10, there was no Congo red staining for native glucagon, even after 28 days.

These Congo red results are helpful in understanding the cytotoxicity results. Cytotoxicity in NIH 3T3 cells was the greatest for high concentrations of glucagon aged in acid (commercial preparation dissolved in HCl), somewhat less for the high concentrations of glucagon aged at pH 8.5, and absent for glucagon prepared at pH 10 in glycine buffer, even at high concentrations. The fact that Congo red binding, which indicates amyloid formation, was highest in the same preparations that led to substantial cytotoxicity suggests that beta sheet amyloid likely contributed to the cytotoxicity. Congo red intensity was very low in the glucagon aged in glycine buffer at pH 10, suggesting stability of the monomer and lack of amyloid formation under this condition. This finding, coupled with the lack of cytotoxicity with the glycine preparation, further support a safety advantage for this condition. Using SEC, there was also much greater preservation of the glucagon monomeric peak over 21 days under the glycine (pH 10) condition as compared to the Tris (pH 8.5) condition or the citrate (pH 3) condition. Studies of glucagon stability may be carried out using reverse-phase high-performance liquid chromatography to evaluate for deamidated compounds and other degradation products.

The studies in nondiabetic pigs revealed a mild delay in the rise of glucagon levels after treatment with aged glucagon, relative to fresh glucagon. The simplest explanation for the delayed rise in plasma glucagon with the aged preparation is the time required for the amyloid to be converted to absorbable monomers or oligomers.

Although most approved drugs have pH values that are lower than the pH 10 preparation described herein, parenteral furosemide has a pH value of approximately 11-12. It is generally well-tolerated when given by intravenous or subcutaneous routes.

The results presented herein underscore that to understand the potential cytotoxicity of glucagon preparations, conditions such as pH and osmolarity must be carefully considered. In general, the conditions that favor cytotoxicity are acid pH and abnormal osmolarity. When the pH of the glucagon buffer during aging is kept at alkaline levels, amyloid formation and cytotoxicity are much lower than at acid pH. The conditions for native glucagon that were most effective in minimizing cell toxicity and amyloid formation were a glycine buffer at pH 10.

E. REFERENCES

1. Pedersen J S, Dikov D, Flink J L, Hjuler H A, Christiansen G, Otzen D E. The changing face of glucagon fibrillation: structural polymorphism and conformational imprinting. J Mol Biol. 2006; 355(3):501-23.
2. Onoue S, Ohshima K, Debari K, Koh K, Shioda S, Iwasa S, Kashimoto K, Yajima T. Mishandling of the therapeutic peptide glucagon generates cytotoxic amyloidogenic fibrils. Pharm Res. 2004; 21(7):1274-83.
3. Castle J R, Engle J M, El Youssef J, Massoud R G, Yuen K C, Kagan R, Ward W K. Novel use of glucagon in a closed-loop system for prevention of hypoglycemia in type 1 diabetes. Diabetes Care. 2010; 33(6)1282-7.
4. El-Khatib F H, Russell S J, Nathan D M, Sutherlin R G, Damiano E R. A bihormonal closed-loop artificial pancreas for type 1 diabetes. Sci Transl Med. 2(27): 27ra27.
5. Ward W K, Engle J, Duman H M, Bergstrom C P, Kim S, I F. The benefit of subcutaneous glucagon during closed-loop glycemic control in rats with type 1 diabetes. IEEE Sensors. 2008; 8(1):89-96.
6. El-Khatib F H, Jiang J, Gerrity R G, Damiano E R. Pharmacodynamics and stability of subcutaneously infused glucagon in a type 1 diabetic swine model in vivo. Diabetes Technol Ther. 2007; 9(2):135-44.
7. Chabenne J R, DiMarchi M A, Gelfanov V M, DiMarchi R D. Optimization of the native glucagon sequence for medicinal purposes J Diabetes Sci Technol. 2010; 4(6); 1322-31.
8. Korzeniewski C, Callewaert D M. An enzyme-release assay for natural cytotoxicity. J Immunol Methods. 1983; 64(3):313-20.
9. Mosmann T. Rapid colorimetric assay for cellular growth and survival: application to proliferation and cytotoxicity assays. J Immunol Methods. 1983; 65(1-2):55-63.
10. Klunk W E, Pettegrew J W, Abraham D J. Quantitative evaluation of congo red binding to amyloid-like proteins with a beta-pleated sheet conformation. J Histochem Cytochem. 1989; 37(8):1273-81.
11. Pedersen J S, Otzen D E. Amyloid-a state in many guises: survival of the fittest fibril fold. Protein Sci. 2008; 17(1): 2-10.
12. Maji S K, Perrin M H, Sawaya M R, Jessberger S, Vadodaria K, Rissman R A, Singru P S, Nilsson K P, Simon R, Schubert D, Eisenberg D, Rivier J, Sawchenko P, Vale W, Riek R. Functional amyloids as natural storage of peptide hormones in pituitary secretory granules. Science. 2009; 325(5938):328-32.
13. Verma A K, da Silva J H, Kuhl D R. Diuretic effects of subcutaneous furosemide in human volunteers: a randomized pilot study. Ann Pharmacother. 2004; 38(4):544-9.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of treating a glucagon-responsive medical condition, comprising:
providing an aqueous solution of glucagon at a pH of greater than about 9;
storing the solution in liquid form at a pH of greater than about 9 for at least three days at room temperature or higher without substantial aggregation of the glucagon; and
delivering at least a portion of the solution into a subject after the step of storing.

2. The method of claim 1, wherein the glucagon is present at a concentration of at least about 0.5 mg/mL.

3. The method of claim 1, wherein the solution is stored at a pH of about 9.5 to 10.5.

4. The method of claim 1, wherein the solution includes a buffering agent comprising an ampholyte.

5. The method of claim 4, wherein the ampholyte is glycine.

6. The method of claim 1, wherein the solution is substantially free of detergent.

7. The method of claim 1, wherein the step of storing is performed in a drug delivery device, and wherein the step of delivering is performed with the drug delivery device.

8. The method of claim 1, wherein the step of delivering is performed by injection intravenously, intramuscularly, or subcutaneously.

9. The method of claim 1, wherein the subject is hypoglycemic.

10. The method of claim 1, wherein the step of delivering is controlled by a processor that is in communication with at least one glucose sensor that monitors glucose concentration of the subject.

11. The method of claim 10, wherein the processor is programmed to cause delivery of the solution based on a proportional error and/or a derivative error of the glucose concentration.

12. The method of claim 11, wherein the timing and amount of glucagon delivered is based on the proportional error and the derivative error.

13. The method of claim 11, wherein the processor is programmed to use a fading memory proportional derivative algorithm to determine the timing and amount of glucagon delivered, based on a signal from the at least one glucose sensor.

14. A drug delivery system, comprising:
a drug delivery device including a container holding an aqueous solution of glucagon that has been stored in the container at a pH of greater than about 9 and at room temperature or higher for at least three days, the glucagon being substantially non-aggregated, the device also including an outlet through which the solution is configured to be driven from the container for delivery into a subject.

15. The drug delivery system of claim 14, further comprising a pressure source operatively disposed to drive the solution from the container through the outlet.

16. The drug delivery system of claim 15, further comprising at least one glucose sensor and a processor programmed to control operation of the pressure source based on a signal received from the glucose sensor.

17. The drug delivery system of claim 16, wherein the processor is programmed to control operation of the pressure source based on a proportional error and/or a derivative error of glucose concentration measured by the glucose sensor.

18. The drug delivery system of claim 17, wherein the processor is programmed to control the timing and amount of glucagon delivered based on the proportional error and the derivative error.

19. The method of claim 1, wherein the step of storing is performed at a pH of greater than about 9 for at least three days at a physiological temperature.

20. The system of claim 14, wherein the solution of glucagon has been stored in the container at a pH of greater than about 9 for at least three days at a physiological temperature.

* * * * *